United States Patent [19]

Angelastro et al.

[11] Patent Number: 4,966,897
[45] Date of Patent: Oct. 30, 1990

[54] 4-SUBSTITUTED 17β-(CYCLOPROPYLOXY)ANDROST-5-EN-3β-OL AND RELATED COMPOUNDS USEFUL AS C17-20 LYASE INHIBITORS

[75] Inventors: Michael R. Angelastro, Loveland; Thomas R. Blohm, Cincinnati, both of Ohio

[73] Assignee: Merrell Dow Pharmaceuticals Inc., Cincinnati, Ohio

[21] Appl. No.: 394,026

[22] Filed: Aug. 15, 1989

[51] Int. Cl.[5] ............................................. A61K 31/56
[52] U.S. Cl. ................................... 514/177; 514/178; 514/182; 552/652
[58] Field of Search ................................. 514/178, 177

[56] References Cited

U.S. PATENT DOCUMENTS 3,475,464 10/1964 Halpern ................................. 514/178
4,139,617 2/1979 Greenwell et al. .................. 514/178

Primary Examiner—Mukund J. Shah
Assistant Examiner—Deborah Carr
Attorney, Agent, or Firm—John J. Kolano

[57] ABSTRACT

This invention is directed to 4-substituted 17β-(cyclopropyloxy)androst-5-en-3β-ols and related compounds and also to a method for using such compounds in the treatment of androgen-dependent disorders. The ethers are prepared by using the Simmons-Smith reaction and an appropriate vinyl ether.

8 Claims, No Drawings

4-SUBSTITUTED 17β-(CYCLOPROPYLOXY)ANDROST-5-EN-3β-OL AND RELATED COMPOUNDS USEFUL AS C17-20 LYASE INHIBITORS

The present invention is directed to 4-substituted 17β-(cyclopropyloxy)androst-5-en-3β-ols and related compounds and also to a method for using such compounds in the treatment of androgen-dependent disorders. More particularly, the present invention is directed to a group of compounds having the following general formula:

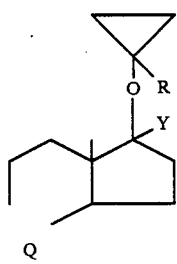

wherein R is hydrogen or methyl; Y is hydrogen or $C_1-C_4$ alkyl; and Q is

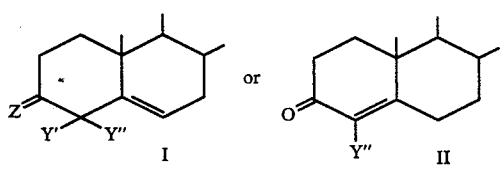

wherein Z is =O, β-OH or β-OZ' wherein Z' is alkanoyl of 1-10 carbon atoms or substituted $C_{2-4}$ alkanoyl wherein the substituent is cyclopentane or benzene; Y' is hydrogen or halogen; and Y" is methyl or halogen. In the above structural formula, Z is shown as a divalent group and, in those definitions of Z which provide for only a single substituent (β), the second valence is occupied by a hydrogen. Examples of the alkanoyl groups containing 1-10 carbon atoms are acetyl, propionyl, butanoyl and decanoyl; examples of the substituted $C_{2-4}$ alkanoyl groups are cyclopentanepropionyl and benzenepropionyl. The halogen atoms referred to above can be fluorine, chlorine or bromine. Preferred compounds are those in which Q has structure I and, more particularly, those compounds in which Q has structure I and Y' and Y" are both halogen. A still further preferred group of compounds are those wherein Q has structure I and Y' and Y" are both fluorine.

Examples of specific compounds of the present invention are the following:

4,4-Difluoro-17β-(cyclopropyloxy)androst-5-en-3β-ol.
4,4-Difluoro-17β-(cyclopropyloxy)androst-5-en-3-one.
4,4-Difluoro-17β-(1-methylcyclopropyloxy)androst-5-en-3β-ol.
4,4-Difluoro-17β-(cyclopropyloxy)-17α-methylandrost-5-en-3β-ol.
4,4-Difluoro-17β-(1-methylcyclopropyloxy)-17α-methylandrost-5-en-3β-ol.
4,4-Dichloro-17β-(cyclopropyloxy)androst-5-en-3β-ol.
4β-Fluoro-17β-(cyclopropyloxy)androst-5-en-3β-ol.
17β-(Cyclopropyloxy)-4β-methylandrost-5-en-3β-ol.
4-Fluoro-17β-(cyclopropyloxy)androst-4-en-3-one
17β-(Cyclopropyloxy)-4-methylandrost-4-en-3-one.

To obtain the ethers of the present invention, a 17-vinyl ether of an appropriate substituted androst-5-en-17β-ol is reacted with methylene iodide and zinc-copper couple in a Simmons-Smith reaction to convert the vinyl ether group to a cyclopropyl ether group. Any functional group present at the 3-position of the androstene is protected appropriately during this reaction, using a protecting group that is readily removed by standard procedures once the cyclopropyl group has been introduced. Thus, a 3β-hydroxy group can be protected by groups such as a t-butyldimethylsilyl ether, a tetrahydropyranyl ether, or an acetate ester. Protection of a 3-keto group is optional and a ketal, such as the ethylenedioxy ketal, can be used. The particular protecting group used can depend on the availability of starting material involved and the convenience of the protecting reaction. To illustrate, when a t-butyldimethylsilyl ether is used as the protecting group, this group can be readily removed, when desired, by treatment of the silyl ether with tetrabutylammonium fluoride. When a silyl ether is used, the process in question can be illustrated by the following reaction.

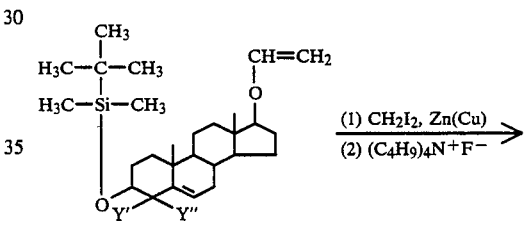

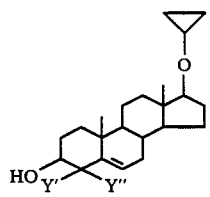

Actually, since the steroid starting material also contains a double bond at the 5-position, a Simmons-Smith reaction can take place at that position in addition to, or instead of, reaction at the 17-vinyl ether double bond. However, the major product obtained is the 17-cyclopropyl ether formed by reaction at the 17-vinyl ether double bond only and any 5,6-cyclopropa-steroids formed by reaction at the 5-double bond are removed during purification.

Although the above procedure can be used to give 3-keto compounds directly, such compounds can also be obtained from an appropriate corresponding 3β-hydroxy compound. Thus, a product 3β-hydroxy cyclopropyl ether can be converted to the corresponding 3-keto-Δ⁵-compound by means of an Oppenauer oxidation using aluminum isopropoxide. For example, oxidation of 4,4-difluoro-17β-(cyclopropyloxy)androst-5-en-3β-ol with aluminum isopropoxide gives 4,4-difluoro-17β-(cyclopropyloxy)androst-5-en-3-one. Conversely, if the 3-ketone is obtained by the original general procedure, that ketone can be reduced using a hydride reducing agent, such as sodium borohydride, to give the corresponding 3β-hydroxy compound. In addition, the corresponding 3-esterified hydroxy compounds can be obtained by reaction of the 3-hydroxy-Δ$^5$-compound with an appropriate acylating agent such as acetic anhydride.

To obtain the vinyl ether starting materials used above, an androst-5-en-17β-ol is reacted with ethyl vinyl ether in the presence of mercuric acetate to give the desired vinyl ether. Any functional group present at the 3-position of the androstene is protected as discussed earlier in connection with the further reaction of the vinyl ether. Compounds useful in this procedure are either known in the art or are readily obtained from known compounds by standard procedures. Thus, for example, 4,4-difluoro-17β-hydroxyandrost-5-en-3-one is reacted with acetyl chloride in an inert solvent such as methylene chloride in the presence of a tertiary amine such as triethyl amine to give the 17-acetate. This ester is then reduced using sodium borohydride in ethanol to give the corresponding 3β-hydroxy compound. Reaction of this alcohol with dihydropyran and hydrochloric acid in methylene chloride gives the corresponding 3-(2-tetrahydropyranyl)oxy steroid. The 17-ester group is then hydrolyzed using lithium hydroxide in a mixture of dioxane and water to give the desired 4,4-fluoro-3-(2-tetrahydropyranyloxy)androst-5-en-17β-ol. In an alternate approach, the 4,4-difluoro-17β-hydroxyandrost-5-en-3-one referred to earlier is reacted with ethylene glycol in ether in the presence of an acid catalyst to give the corresponding 3,3-ethylenedioxy compound and the hydroxy group in that compound is then reacted to give the 17-cyclopropyl ether by the procedures described earlier. Similar procedures can be used to obtain compounds having only one methyl or one halogen substituent at the 4-position.

The present compounds are useful as inhibitors of steroid $C_{17-20}$ lyase. The steroid $C_{17-20}$ lyase enzyme catalyzes the conversion of the $C_{21}$ steroids pregnenolone and progesterone to the $C_{19}$ steroids dehydroepiandrosterone and androstenedione, which are the precursors of the androgens, testosterone and 5α-dihydrotestosterone. Androstenedione and testosterone, in turn, are the precursors of the estrogens, estrone and estradiol. Thus, inhibition of $C_{17-20}$ lyase by the present compounds can reduce formation of the estrogens as well as the androgens. Consequently, the present compounds are useful for treating various androgen-dependent disorders. The present invention thus also encompasses a method for treating androgen-dependent disorders which comprises administering to an individual suffering from such a disorder an effective amount of a compound of the present invention. More particularly, the present compounds are useful in the treatment of prostatic carcinoma, benign prostatic hyperplasia, male-pattern baldness and virilism and hirsutism (in women). The compounds are also useful in the treatment of estrogen-dependent diseases, such as estrogen-dependent breast cancer.

It is well established that reduction of serum testosterone levels is useful in the treatment of many cases of prostatic carcinoma. In clinical practice, this has been accomplished by orchiectomy or by diethylstilbestrol treatment but the first approach is often psychologically unacceptable while a number of side effects are associated with the second approach. Thus, an alternative approach to testosterone reduction is desirable and this can be accomplished by the administration of the present compounds. To the extent that prostatic carcinoma is androgen-dependent, the present compounds would block the source of androgens and thus serve as an appropriate treatment for this condition.

The activity of the present compounds as inhibitors of steroid $C_{17-20}$ lyase is established using microsomal preparations of the steroid $C_{17-20}$ lyase enzyme from human or laboratory animal testes; human testes used for this purpose are obtained from therapeutic orchiectomies. The enzyme is incubated with NADPH and the test compound in the concentration range $5 \times 10^{-8}$M to $3 \times 10^{-6}$M and the extent of inhibition of the enzyme is determined with time-dependency of inhibition being established by a decline in enzyme activity with the time of exposure to the test compound. Time-dependency of inhibition often implies irreversible inactivation of the enzyme and irreversibility is specifically established by inability to restore enzyme activity by dialysis under conditions which maintained activity of native enzyme.

In the treatment of the various androgen-dependent disorders described earlier, the compounds of the present invention may be administered orally to the patient being treated to achieve the particular effect desired. The amount of compound to be administered will vary over a wide range and can be any effective amount. Depending on the patient to be treated, and the severity of the condition being treated, the effective amount of compound administered will vary from about 0.625 to 62.5 mg/kg of body weight per day and preferably from 5 to 30 mg/kg of body weight per day. Unit dosages for oral administration may contain, for example, from 25 to 500 mg of a compound of the invention. Alternatively, the present compounds can be administered by parenteral routes or by implants.

In practicing the method of this invention, the active ingredient is preferably incorporated in a composition containing a pharmaceutical carrier and from about 5 to about 90% by weight of the steroid active ingredient. The term "phamaceutical carrier" refers to known pharmaceuticals excipients useful in formulating pharmaceutically active compounds for internal administration to animals, and which are substantially non-toxic and non-sensitizing under conditions of use. The compositions can be prepared by known techniques for the preparation of tablets or capsules and can contain suitable excipients known to be useful in the preparation of the particular type of composition desired. Suitable pharmaceutical carriers in formulation techniques are found in standard texts, such as *Remingtons Pharmaceutical Sciences*, Mack Publishing Company, Easton, Pa.

The following examples are presented to illustrate the present invention but they should not be construed as limiting it in any way.

EXAMPLE 1

To a solution of 4 g of 4,4-difluoro-3β-(2-tetrahydropyranyloxy)androst-5-en-17β-ol in 50 ml of vinyl ethyl ether, there is added 0.25 g of mercuric acetate. The mixture is stirred at room temperature for 24 hours, quenched with triethylamine, and then poured into dilute aqueous potassium carbonate solution. The aqueous mixture is extracted three times with 100-ml portions of diethyl ether and the combined organic extracts are washed with saturated aqueous sodium chloride solution and then dried over sodium sulfate. The solvent is then removed under reduced pressure and the residue is purified by flash chromatography to give 4,4- difluoro-3β-(2-tetrahydropyranyloxy)-17β-ethenyloxyandrost-5-ene.

EXAMPLE 2

To a suspension of 0.3 g of zinc dust in 3 ml of diethyl ether is added 50 mg of cuprous chloride. The resulting mixture is refluxed for 30 minutes and then 1.06 g of diiodomethane is added. The resulting solution is refluxed for 30 minutes and 0.3 g of 4,4-difluoro-3β-(2-tetrahydropyranyloxy)-17β-ethenyloxyadrost-5-ene is added. The resulting mixture is refluxed for 16 hours and then diluted with 10 ml of diethyl ether and filtered. The solid which is separated is washed with ethyl acetate (3 times, 50 ml) and the combined filtrate and washings are washed with saturated aqueous ammonium chloride and dried over magnesium sulfate. The solvent is then removed under reduced pressure to leave a residual solid which is crude 4,4-difluoro-3β-(2-tetrahydropyranyloxy)-17β-(cyclopropyloxy)androst-5-ene containing some 17β-(cyclopropyloxy)cycloprop[5,-6]androstane product. This material is treated with a catalytic amount of hydrochloric acid in aqueous dioxane to remove the tetrahydropyranyl protecting group. The solvent is then removed under reduced pressure to leave a residual crude solid which is purified by reverse phase high-pressure liquid chromatography to give 4,4-difluoro-17β-(cyclopropyloxy)androst-5-en-3β-ol. The compound has the following structural formula:

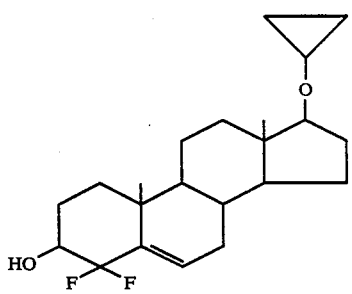

EXAMPLE 3

If the procedure of Example 1 is repeated using 2-propenyl ethyl ether instead of the vinyl ethyl ether and the resulting product is reacted with diiodomethane and zinc-copper couple as described in Example 2, the product obtained is 4,4-difluoro-17β-(1-methylcyclopropyloxy) androst-5-en-3β-ol.

Similarly, 4,4-difluoro-3β-(2-tetrahydropyranyloxy)-17α-methylandrost-5-en-17β-ol is reacted with vinyl ethyl ether according to the procedure described in Example 1 and the resulting product is reacted with diiodomethane and zinc copper couple as described in Example 2. The product obtained in this way is 4,4-difluoro-17α-methyl-17β-(cyclopropyloxy)androst-5-en-3β-ol.

EXAMPLE 4

4,4-Difluoro-17β-(cyclopropyloxy)androst-5-en-3β-ol is treated with acetic anhydride and pyridine. The mixture is poured into water and extracted with ethyl acetate. The ethyl acetate layer is separated and dried and the solvent is evaporated to leave as a residue, 3β-acetyloxy-4,4-difluoro-17β-(cyclopropyloxy)androst-5-ene. 3β-(Cyclopentanepropionyloxy)-4,4-difluoro-17β-(cyclopropyloxy)androst-5-ene and 3β-(benzenepropionyloxy)-4,4-difluoro-17β-(cyclopropyloxy)androst-5-ene are obtained in a similar way using the appropriate acid chlorides.

EXAMPLE 5

A solution of 1.5 grams of 4,4-difluoro-17β-(cyclopropyloxy)androst-5-en-3β-ol in 80 ml of toluene is concentrated to 75% of its original volume and 20 ml of cyclohexanone is added. The mixture is again concentrated to 75% of its volume and 1.5 g of aluminum isopropoxide is added. The reaction mixture is refluxed for 45 minutes, cooled to room temperature, and 50 ml of water and 5 ml of concentrated hydrochloric acid are added. The solution is then treated with 11 g of sodium hydroxide and the two phases are separated. The aqueous phase is extracted with 50 ml of ethyl acetate and the combined organic extracts are dried over sodium sulfate. The solvent is removed in vacuo and the residue is recrystallized to give 4,4-difluoro-17β-(cyclopropyloxy)androst-5-en-3-one.

What is claimed is:

1. A compound of the formula:

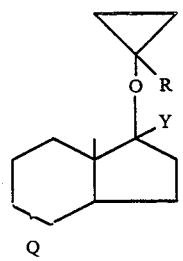

wherein R is hydrogen or methyl; Y is hydrogen or $C_1$-$C_4$ alkyl; and Q is

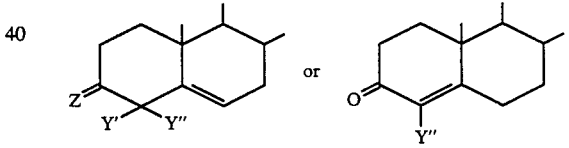

wherein Z is =O, β-OH or β-OZ' wherein Z' is alkanoyl of 1-10 carbon atoms or substituted $C_{2-4}$ alkanoyl wherein the substituent is cyclopentane or benzene; Y' is hydrogen or halogen; and Y'' is methyl or halogen.

2. A compound according to claim 1 which has the formula:

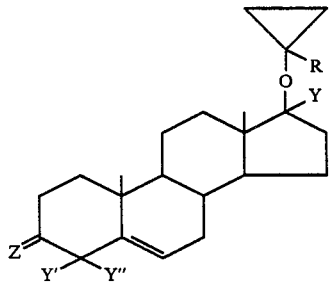

wherein Z is =O, β-OH or β-OZ' wherein Z' is alkanoyl of 1-10 carbon atoms of substituted $C_{2-4}$ alkanoyl wherein the substituent is cyclopentane or benzene; R is hydrogen or methyl; Y is hydrogen or $C_1$-$C_4$ alkyl; Y' is halogen; and Y" is methyl or halogen.

3. A compound according to claim 1 which has the formula:

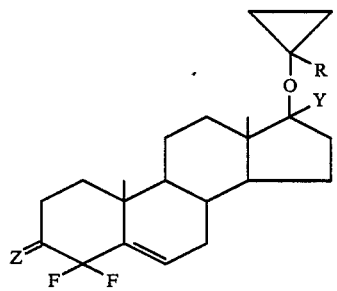

wherein Z is =O, β-OH or β-OZ' wherein Z' is alkanoyl of 1-10 carbon atoms or substituted $C_{2-4}$ alkanoyl wherein the substituent is cyclopentane or benzene; R is hydrogen or methyl; and Y is hydrogen or $C_1$-$C_4$ alkyl.

4. A compound according to claim 1 which is 4,4-difluoro-17β-(cyclopropyloxy)androst-5-en-3β-ol.

5. A compound according to claim 1 which is 4,4-difluoro-17β-(cyclopropyloxy)androst-5-en-3-one.

6. A method for treating androgen-dependent disorders which comprises administering to an individual suffering from such a disorder an effective amount of a compound of the formula:

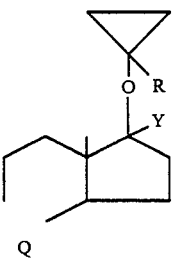

wherein R is hydrogen or methyl; Y is hydrogen or $C_1$-$C_4$ alkyl; and Q is

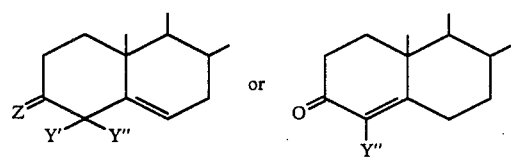

wherein Z is =O, β-OH or β-OZ' wherein Z' is alkanoyl of 1-10 carbon atoms or substituted $C_{2-4}$ alknaoyl wherein the substituent is cyclopentane or benzene; Y' is hydrogen or halogen; and Y" is methyl or halogen.

7. A method according to claim 6 which comprises administering an effective amount of a compound of the formula:

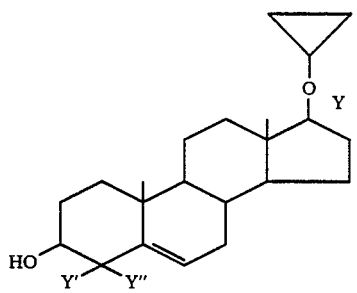

wherein Y is hydrogen or $C_1$-$C_4$ alkyl; Y' is halogen; and Y" is methyl or halogen.

8. A method according to claim 6 which comprises administering an effective amount of 4,4-difluoro-17β-(cyclopropyloxy)-androst-5-en-3β-ol.

* * * * *